`US009861721B2`

(12) United States Patent
Stokes et al.

(10) Patent No.: US 9,861,721 B2
(45) Date of Patent: *Jan. 9, 2018

(54) SYSTEMS AND METHODS FOR PERFORMING THE BACTERIAL DISINFECTION OF A FLUID USING POINT RADIATION SOURCES

(71) Applicants: University of North Carolina at Charlotte, Charlotte, NC (US); AquiSense Technologies LLC, Walton, KY (US)

(72) Inventors: Edward Brittain Stokes, Charlotte, NC (US); Jennifer Godwin Pagan, Charlotte, NC (US); Thomas Andrew Schmedake, Charlotte, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 15/631,050

(22) Filed: Jun. 23, 2017

(65) Prior Publication Data
US 2017/0290943 A1    Oct. 12, 2017

Related U.S. Application Data

(63) Continuation of application No. 13/163,055, filed on Jun. 17, 2011, which is a continuation of application No. PCT/US2009/068765, filed on Dec. 18, 2009.
(Continued)

(51) Int. Cl.
| *A61L 9/20* | (2006.01) |
| *C02F 1/32* | (2006.01) |
| *G01N 21/33* | (2006.01) |

(52) U.S. Cl.
CPC .............. *A61L 9/205* (2013.01); *C02F 1/325* (2013.01); *A61L 2209/11* (2013.01);
(Continued)

(58) Field of Classification Search
CPC ....... C02F 2303/04; C02F 1/325; A61L 9/205
See application file for complete search history.

(56) References Cited

U.S. PATENT DOCUMENTS

| 5,874,741 A | 2/1999 | Matschke |
| 6,118,134 A | 9/2000 | Justak |
| (Continued) | | |

FOREIGN PATENT DOCUMENTS

| EP | 1843401 A1 | 10/2007 |
| EP | 1887297 A1 | 2/2008 |
| WO | WO2009021108 A1 | 2/2009 |

OTHER PUBLICATIONS

US 9,750,836, 09/2017, Stokes (withdrawn)*
(Continued)

*Primary Examiner* — Patrick Orme
(74) *Attorney, Agent, or Firm* — Hasse & Nesbitt LLC; Donald E. Hasse (57) ABSTRACT

A system for disinfecting a fluid, including: a flow cell including one or more inlet ports and one or more outlet ports, wherein the flow cell is configured to communicate a fluid containing a biological contaminant from the one or more inlet ports to the one or more outlet portions through an interior portion thereof; and one or more point radiation sources disposed about the flow cell, wherein the one or more point radiation sources are operable for delivering radiation to the biological contaminant; wherein an interior surface of the flow cell is operable for reflecting the radiation delivered to the biological contaminant by the one or more point radiation sources; and wherein the interior surface of the flow cell is operable for reflecting the radiation delivered to the biological contaminant by the one or more point radiation sources such that a radiation intensity is uniform throughout the interior portion of the flow cell. In one exemplary embodiment, the flow cell is an integrating sphere. Optionally, the system also includes a photocatalyzing material disposed on at least a portion of the interior surface of the flow cell.

17 Claims, 2 Drawing Sheets

Related U.S. Application Data (60) Provisional application No. 61/139,022, filed on Dec. 19, 2008.

(52) U.S. Cl.
CPC .. *C02F 2201/326* (2013.01); *C02F 2201/328* (2013.01); *C02F 2201/3222* (2013.01); *C02F 2201/3225* (2013.01); *C02F 2201/3227* (2013.01); *C02F 2201/3228* (2013.01); *C02F 2303/04* (2013.01); *C02F 2305/10* (2013.01); *G01N 21/33* (2013.01); *G01N 2201/065* (2013.01)

(56) References Cited

U.S. PATENT DOCUMENTS

| | | | |
|---|---|---|---|
| 6,555,011 B1* | 4/2003 | Tribelsky | A61L 2/08 204/158.2 |
| 7,259,846 B2 | 8/2007 | Schembri | |
| 7,554,109 B2 | 6/2009 | Stokes | |
| 2003/0194692 A1 | 10/2003 | Purdum | |
| 2005/0274663 A1 | 12/2005 | Roitman | |
| 2009/0269868 A1 | 10/2009 | Stokes | |
| 2012/0318749 A1 | 12/2012 | Stokes | |
| 2014/0161664 A1 | 6/2014 | Harris et al. | |
| 2014/0240695 A1 | 8/2014 | Pagan et al. | |

OTHER PUBLICATIONS

U.S. Appl. No. 13/163,055, filed JUn. 17, 2011, Stokes et al.
U.S. Appl. No. 14/102,969, filed Dec. 11, 2013, Harris et al.
U.S. Appl. No. 14/271,859, filed May 7, 2014, Pagan et al.
Pagan et al., PCT/US2011/025197, Feb. 17, 2011.
Fry, Katatwar, and Pope, "Integrating Cavity Absorption Meter", Applied Optics, Apr. 20, 1992, pp. 2055-2065, 31 (12).
Elterman, "Integrative Cavity Spectroscopy", Applied Optics, Sep. 1970, pp. 2140-2142, 9(9).
Goebel, "Generalized Integrating-Sphere Theory", Applied Optices, Jan. 1967, pp. 125-128, 6(1).
Winston, Minano, Benitez, "Nonimaging Optics", Elsevier Academic Press, 2005, Chapter 4.1 Limits to Concentration.
Karagodsky et al., "Theoretical Analysis of Subwavelength High Contrast Grating Reflectors", Optics Express, Jul. 26, 2010, pp. 16973-16988, 18(16).
Frear et al., "Structure and Properties of Al-1%Si Thin Films on Si as a Function of Gas Inpurities During DC Magnetron-Sputtered Deposition", Journal of Electronic Materials, 1989, pp. 517-525, 18(4).
Rode, Gaddam and Yi, "Subnanometer surface roughness of dc Magnetron Puttered Al films", J. Appl. Phys., 2007, pp. 024303-1-0243038, 102.
Ocean Optics, STAN Series Reflectance Standards, http://oceanoptics.com/product/stan-series-refectance-standards/.
Ocean Optics, WS-1 Reflectance Standards, http://oceanoptics.com/product/ws-1-refectance-standards/.
Wladyslaw Kowalski, "Ultraviolet Germicidal Irradiation Handbook", Appendix F: Ultraviolet Material Reflectivities (UVC/UVB Range), Springer, p. 491.
Linden, Karl, et al., "Ultraviolet disinfection of marginal effluents: determining ultraviolet absorbance and subsequent estimation of ultraviolet intensity," 1998, Water Environment Research, vol. 70, No. 2, 214-223.
Javorfi, Tames, et al., "Quantitative spectrophotometry using integrating cavities," 2006, J. of Photochemistry & Photobiology B: Biology, 82:127-131.

\* cited by examiner

SYSTEMS AND METHODS FOR PERFORMING THE BACTERIAL DISINFECTION OF A FLUID USING POINT RADIATION SOURCES

CROSS-REFERENCE TO RELATED APPLICATION(S)

This application is a continuation of U.S. application Ser. No. 13/163,055, filed Jun. 17, 2011, which is a continuation of International Application PCT/US2009/068765, filed Dec. 18, 2009, which claims the benefit of U.S. Provisional Application 61/139,022, filed Dec. 19, 2008, the disclosures of which are incorporated herein by reference.

STATEMENT REGARDING FEDERALLY-SPONSORED RESEARCH OR DEVELOPMENT

The U.S. Government has a paid-up license in the present invention and the right, in limited circumstances, to require the patent owner to license to others on reasonable terms as provided for by the terms of Award Nos. 0740524 and 0848759 awarded by the National Science Foundation (NSF).

FIELD OF THE INVENTION

The present invention relates to systems and methods for performing the bacterial disinfection of a fluid using point radiation sources and encompasses the fields of optical engineering, fluid engineering, materials engineering, and the biological sciences.

BACKGROUND OF THE INVENTION

Conventionally, the bacterial disinfection of fluids, such as water, air, fuel, other liquids and gases, and the like, is performed using ultraviolet (UV) lamps (or deep-UV lamps), such as low to medium pressure mercury lamps. For example, water may be disinfected using such lamps, for a germicidal effect, in a conventional point-of-use (POU) water filtration system. The deoxyribonucleic acid (DNA) of bacteria, viruses, cysts, and the like absorbs the UV radiation and the reproductive capabilities of the biological entities are thereby deactivated. Unlike chlorinated methods of water disinfection, the UV radiation does not impact the biological stability of the water. Thus, UV assisted water filtration has become a standard practice for germicidal benefit in water filtration systems, including the large reactors used in public water systems (PWSs), as well as the small POU water filtration systems. Comparable bacterial disinfection systems are used in conjunction with other fluids.

These bacterial disinfection systems, however, suffer from a number of significant shortcoming. First, the bacterial disinfection systems, because they use tubular UV lamps or the like, typically have high power requirements and large form factors, requiring that they utilize line voltage, represent separate components from associated fluid filtration systems, are not compatible with smaller form factor POU fluid filtration systems, and/or are not arbitrarily scalable. Second, the bacterial disinfection systems are inherently inefficient. The tabular UV lamps used emit photons that pass through the fluid and are absorbed by another surface or reflected once or twice and lost. The result is that photons must continually be generated and replaced. Further, the radiation field present is not uniform. High intensity is typically used in lamp based systems to compensate for losses and non-uniform radiation fields. Thus, what is still needed in the art is an improved bacterial disinfection system that addresses these shortcomings and provides other advantages.

BRIEF SUMMARY OF THE INVENTION

Again, the present invention relates to systems and methods for performing the bacterial disinfection of a fluid using point radiation sources. Generally, these systems and methods utilize one or more point radiation sources that are arranged around the interior of an integrating sphere flow-through cell, also referred to herein as a flow-through integrating sphere (FIS), or the like. Preferably, the one or more point radiation sources are UV optical sources, and optionally the one or more point radiation sources are deep-UV optical sources, such as semiconductor or light-emitting diode (LED) optical sources. The one or more point radiation sources are operable to disinfect a fluid selectively exposed to them as the DNA of bacteria, viruses, cysts, and the like in the fluid absorbs the radiation generated and reflected in the integrating sphere flow-through cell or the like and the biological entities are thereby deactivated. Optionally, the interior of the integrating sphere flow-through cell or the like is coated with a Lambertian scattering material, and/or with a photocatalytic material capable of destroying adsorbed biological materials in the presence of the generated and reflected radiation, and/or with a photocatalytic capable of generating a disinfecting agent in the presence of the generated and reflected radiation.

In one exemplary embodiment, the present invention provides a system for disinfecting a fluid, including: a flow cell including one or more inlet ports and one or more outlet ports, wherein the flow cell is configured to communicate a fluid from the one or more inlet ports to the one or more outlet portions through an interior portion thereof; and one or more point radiation sources disposed about the flow cell, wherein the one or more point radiation sources are operable for delivering radiation to the fluid; wherein an interior surface of the flow cell is operable for reflecting the radiation delivered to the fluid by the one or more point radiation sources. In one exemplary embodiment, the flow cell is an integrating sphere. Optionally, the one or more point radiation sources include one or more of one or more semiconductor optical sources, one or more light-emitting diode optical sources, one or more ultraviolet optical sources, and one or more deep-ultraviolet optical sources. The interior surface of the flow cell is operable for reflecting the radiation delivered to the fluid by the one or more point radiation sources such that a radiation intensity is uniform throughout the interior portion of the flow cell. Optionally, the system also includes one or more mechanical baffles or stirring mechanisms disposed within the interior portion of the flow cell for selectively modifying a flow of the fluid therethrough. Optionally, the system further includes a photocatalyzing material disposed on at least a portion of the interior surface of the flow cell. Optionally, the system still further includes a photocatalyzing material disposed on at least a portion of a surface of the one or more mechanical baffles or stirring mechanisms. Preferably, the system includes a controller operable for selectively activating/deactivating the one or more point radiation sources and a controller operable for selectively controlling the residence time of the fluid in the interior portion of the flow cell.

In another exemplary embodiment, the present invention provides a method for disinfecting a fluid, including: providing a flow cell including one or more inlet ports and one or more outlet ports, wherein the flow cell is configured to communicate a fluid from the one or more inlet ports to the one or more outlet portions through an interior portion thereof; and providing one or more point radiation sources disposed about the flow cell, wherein the one or more point radiation sources are operable for delivering radiation to the fluid; wherein an interior surface of the flow cell is operable for reflecting the radiation delivered to the fluid by the one or more point radiation sources. In one exemplary embodiment, the flow cell is an integrating sphere. Optionally, the one or more point radiation sources include one or more of one or more semiconductor optical sources, one or more light-emitting diode optical sources, one or more ultraviolet optical sources, and one or more deep-ultraviolet optical sources. The interior surface of the flow cell is operable for reflecting the radiation delivered to the fluid by the one or more point radiation sources such that a radiation intensity is uniform throughout the interior portion of the flow cell. Optionally, the method also includes providing one or more mechanical baffles or stirring mechanisms disposed within the interior portion of the flow cell for selectively modifying a flow of the fluid therethrough. Optionally, the method further includes providing a photocatalyzing material disposed on at least a portion of the interior surface of the flow cell. Optionally, the method still further includes providing a photocatalyzing material disposed on at least a portion of a surface of the one or more mechanical baffles or stirring mechanisms. Preferably, the method includes providing a controller operable for selectively activating/deactivating the one or more point radiation sources and a controller operable for selectively controlling the residence time of the fluid in the interior portion of the flow cell.

In a further exemplary embodiment, the present invention provides a system for disinfecting a fluid, including: a flow cell including one or more inlet ports and one or more outlet ports, wherein the flow cell is configured to communicate a fluid comprising a biological contaminant from the one or more inlet ports to the one or more outlet portions through an interior portion thereof; and one or more point radiation sources disposed about the flow cell, wherein the one or more point radiation sources are operable for delivering radiation to the biological contaminant; wherein an interior surface of the flow cell is operable for reflecting the radiation delivered to the biological contaminant by the one or more point radiation sources; and wherein the interior surface of the flow cell is operable for reflecting the radiation delivered to the biological contaminant by the one or more point radiation sources such that a radiation intensity is uniform throughout the interior portion of the flow cell. In one exemplary embodiment, the flow cell is an integrating sphere. Optionally, the one or more point radiation sources include one or more of one or more semiconductor optical sources, one or more light-emitting diode optical sources, one or more -ultraviolet optical sources, and one or more deep-ultraviolet optical sources. Optionally, the system also includes a photocatalyzing material disposed on at least a portion of the interior surface of the flow cell.

BRIEF DESCRIPTION OF THE DRAWINGS

The present invention is illustrated and described herein with reference to the various drawings, in which like reference numbers are used to denote like system components/method steps, as appropriate, and in which.

DETAILED DESCRIPTION OF THE INVENTION

Again, the present invention relates to systems and methods for performing the bacterial disinfection of a fluid using point radiation sources. Generally, these systems and methods utilize one or more point radiation sources that are arranged around the interior of an integrating sphere flow-through cell, also referred to herein as a FIS, or the like. Preferably, the one or more point radiation sources are UV optical sources, and optionally the one or more point radiation sources are deep-UV optical sources, such as semiconductor or LED optical sources. The one or more point radiation sources are operable to disinfect a fluid selectively exposed to them as the DNA of bacteria, viruses, cysts, and the like in the fluid absorbs the radiation generated and reflected in the integrating sphere flow-through cell or the like and the biological entities are thereby deactivated. Optionally, the interior of the integrating sphere flow-through cell or the like is coated with a Lambertian scattering material and/or with a material that undergoes photocatalysis, thereby locally generating a disinfecting agent in the presence of the generated and reflected radiation.

As a preliminary matter, it should be noted that the bacterial disinfection systems and methods of the present invention are illustrated and described herein largely in connection with an application involving the disinfection of polished water in a commercial under-sink water filtration unit. This specific application is exemplary only and should not be construed to be limiting in any manner. The bacterial disinfection systems and methods of the present invention may be generalized and utilized in any fluid disinfection application, including, but not limited to, the bacterial disinfection of water, air, fuel, other fluids and gases, and the like. Thus, the bacterial disinfection systems of the present invention are robust and encompass a wide variety of applications and industries. They are also scalable in size and scope.

Figure 1:
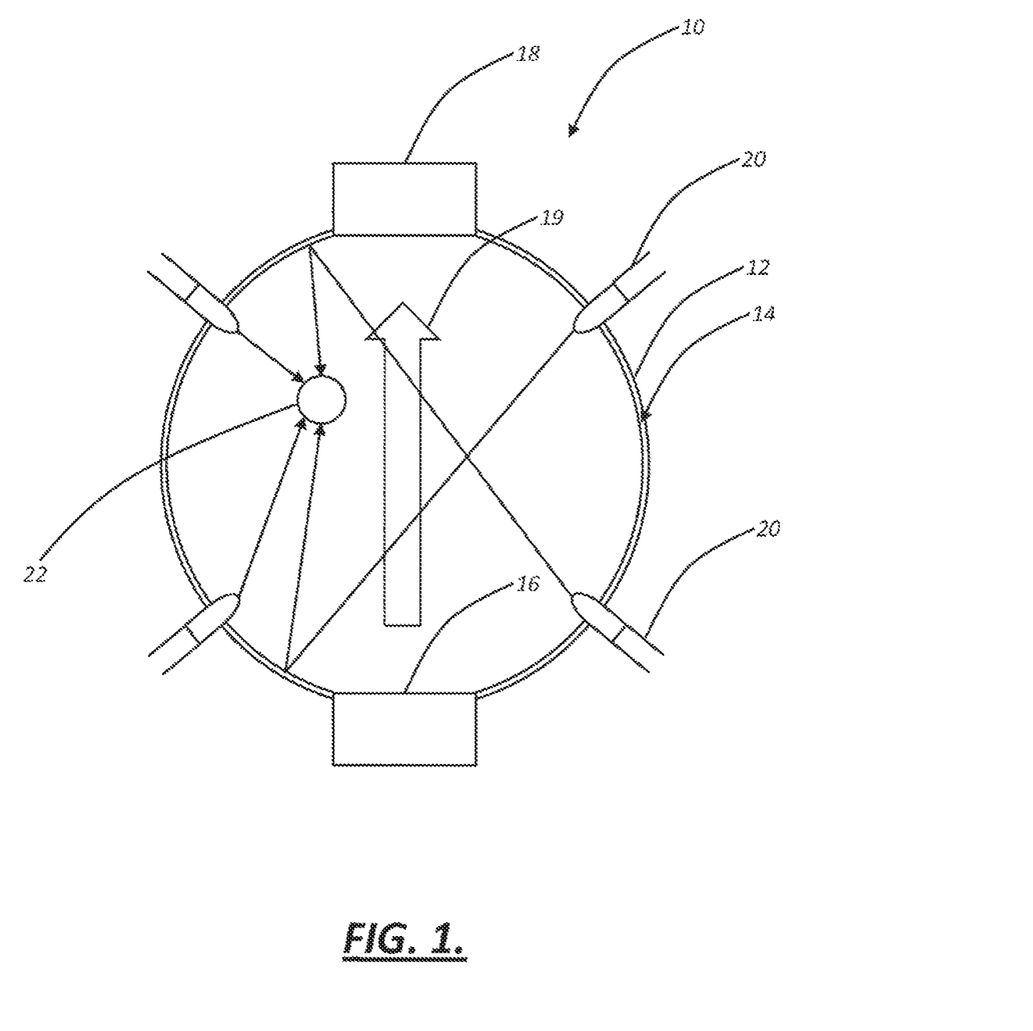
FIG. 1 is a schematic diagram illustrating one exemplary embodiment of the integrating sphere point radiation source fluid disinfection system of the present invention.

Referring to FIG. 1, in one exemplary embodiment, the disinfection system 10 of the present invention includes a flow cell 12 that takes the form of an integrating sphere or the like. Although the integrating sphere configuration is discussed at length herein, other configurations may also be utilized. The key consideration is that photons are repeatedly reflected within the flow cell 12 and that a uniform radiation field is formed for optimal disinfection with low intensity sources. Along these lines, the flow cell 12 should have substantially curved and concave opposed interior surfaces. To restate, the flow cell 12 must not have internal "corners," and every point on the interior surface should be visible front every other point on the interior surface. Ovoids, ellipsoids, cubes with rounded corners, etc. all fit these criteria. The flow cell 12 is made of plastic or the like for ease of manufacturing, and, in such cases where the material is not a good Lambertian scatterer, the interior surfaces thereof are coated with a Lambertian scattering material 14. Alternatively, the flow cell 12 is made of a metallic or other reflective or coated reflective material, such as aluminum, stainless steel, copper, etc., which may be anodized or otherwise coated with organic polymer, silicone, inorganic oxide, etc. The flow cell 12 is scalable and may have any suitable dimensions, on the order of millimeters to meters, for example.

The flow cell 12 includes at least an inlet port 16 and an outlet port 18 manufactured into it that provides for the flow of a fluid 19 (i.e. a liquid or gas) from the inlet port 16 to the outlet port 18. It will be readily apparent to those of ordinary skill in the art that multiple inlet ports 16 and/or multiple outlet ports 18 may also be utilized. Preferably, the fluid 19 is not allowed to stagnate in any portion of the interior of the flow cell 12 for an appreciable period of time, as described in greater detail herein below, and the flow cell 12 is kept 100% full at all times. Likewise, it may be desirable that the fluid 19 be directed towards one or more interior surfaces of the flow cell 12, such that a disinfecting agent generated by a photocatalyzing material may be encountered, as also described in greater detail herein below.

In the nominal design, one or more point radiation sources 20, such as one or more UV optical sources, one or more deep-UV optical sources, one or more semiconductor optical sources, and/or one or more LED optical sources, are disposed within or partially or wholly through one or more ports (not illustrated) manufactured through the flow cell 12, preferably at symmetric positions. The one or more point radiation sources 20 are operable to disinfect the fluid 19 that is selectively exposed to them as the DNA of bacteria, viruses, cysts, and the like 22 in the fluid 19 absorbs the radiation generated and reflected in the flow cell 12 and the biological entities are thereby deactivated. "Point radiation sources" as used herein refer to small, roughly symmetrical radiation sources as compared to the other dimensions of the system.

Figure 2:
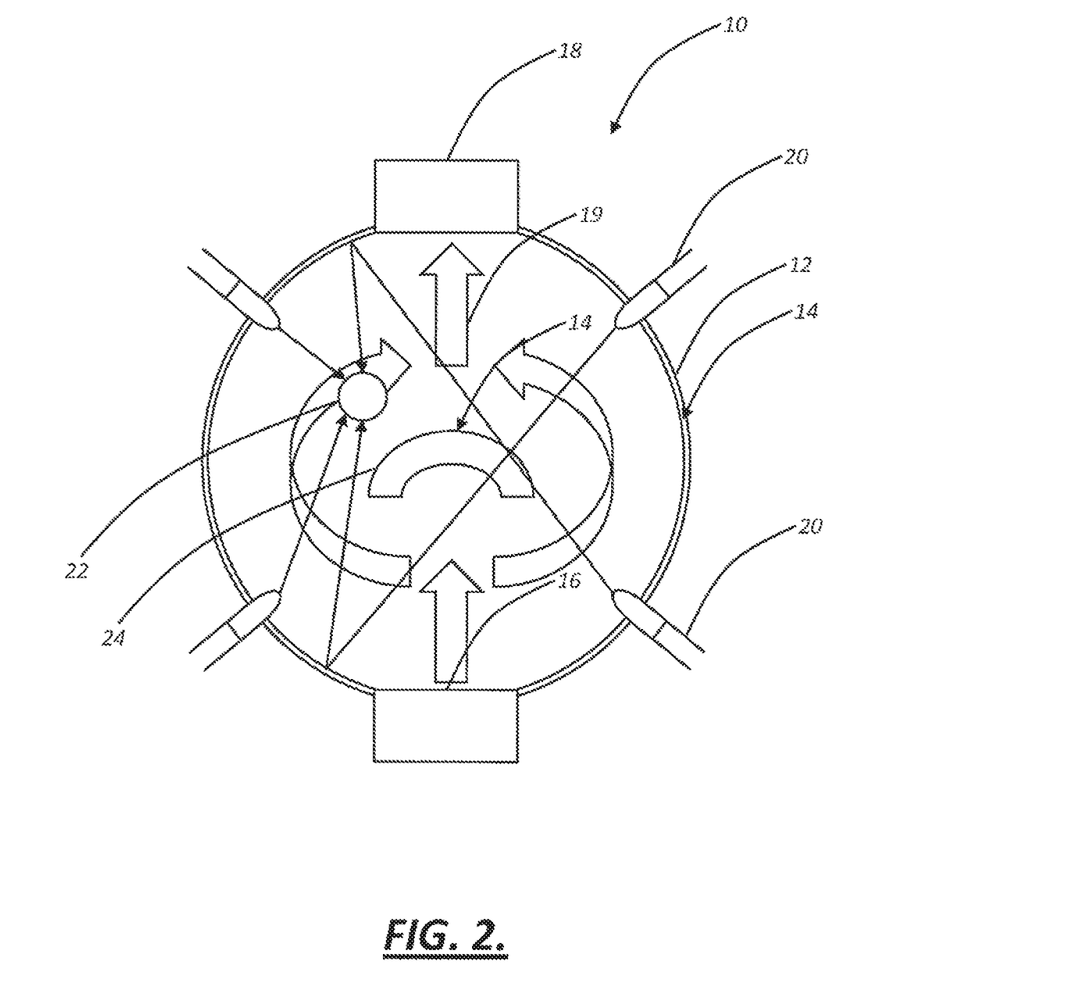
FIG. 2 is a schematic diagram illustrating another exemplary embodiment of the integrating sphere point radiation source fluid disinfection system of the present invention.

Referring to FIG. 2, in another exemplary embodiment, the disinfection system 10 of the present invention includes one or more mechanical baffles 24, mechanical stirring mechanisms, or the like, also optionally coated with Lambertian scattering material 14 and/or photocatalyzing material. This configuration is used to equilibrate and maximize the residence time of the fluid 19 in the interior volume of the flow cell 12. When a bacterium or the like 22 is in the interior volume of the flow cell 12, the goal is to optimize the design parameters (i.e. sizes of the flow cell 12, reflectance of Lambertian scattering material 14, residence time, and the radiant power of the one or more point radiation sources 20) to ensure that the bacterium or the like 22 receives a lethal dose of UV radiation while it is in the flow cell 12.

Optionally, a photocatalytic material 14, such as titanium dioxide ($TiO_2$), zinc oxide, zirconium dioxide, iron oxide, aluminum oxide, $Fe(III)Al_2O_3$, cerium oxide, manganese oxide, titanium silicates, metal substituted silicates or aluminosilicates, and any other metal oxide, mixed metal oxide, and/or metal doped/supported metal oxide substrates (e.g. gold nanoparticles supported on silicon dioxide or titanium dioxide), or the like, may be disposed on the inner surface(s) of the flow cell 12 or otherwise integrated with these surfaces to enhance the photo-oxidation, photo-reduction, and decontamination of contaminants on a near-field basis, including bacteria, pathogens, organic materials, halogenated compounds, biogenic compounds, metal ions, and/or biological agents. Alternatively, the photocatalyst material 14 could be suspended on a non-absorbing substrate (such as a fiber or a mesoporous or macro-porous sol-gel, ormisil, polymer, or aerogel) which occupies some of the interior region of she flow cell 12. This would provide uniform illumination of the catalyst from all directions for optimal photocatalytic rates due to the unique highly reflective and randomizing nature of the integrating sphere surface. A flow detector (not illustrated) or the like may be used before or after the flow cell 12 to turn off the one or more point radiation sources 20 during periods of no flow to maximize the life of the one or more point radiation sources 20, and the entire system may be coupled to an appropriate computer controller/processor (not illustrated) or the like that controls the overall function of the disinfection system 10.

As a preliminary matter, DNA has peak absorption at about 260 nm, but the absorption curve is broad, with the majority of UV absorption occurring between about 240 nm and about 280 nm. Low and medium pressure mercury lamps have emission peaks at about 253.7 nm, with medium pressure lamps having emission peaks which are narrow and sporadic across the peak microbicidal region of DNA. In comparison, UV LEDs have broadband deep-UV emission and may be tailored for peak emission at about 260 nm to provide the maximum dose more effectively than mercury lamps. The LED wavelength may be shifted by varying the percent composition of aluminum within the $Al_xGa_{(1-x)}N$ active layer of the LED. LEDs with wavelengths centered at the peak of DNA absorption are recently commercially available. In addition, UV LEDs contain no mercury, which is extremely toxic such that discharge lamps containing mercury must be treated as hazardous waste and sent to as approved recycling facility when spent. Also, mercury based sources produce emission lines at about 185 nm, which results in ozone production; ozone is corrosive and absorbs UV light, as well as being toxic. UV LEDs are mercury free solid state sources and may be manufactured to have no emission shorter than about 200 nm. In addition to being mercury free, UV LEDs have some distinct advantages over lamp sources. Lamps are bulky and require line voltage which is undesirable in POU systems, where line voltage is not always available where the unit would be positioned. Also, mercury lamps have a start-up delay time associated with the creation of the plasma in the lamp envelop, which in turn heats the inert gas, which then vaporizes the mercury allowing the mercury and plasma ions to collide and excite the Hg to emission. In contrast, UV LEDs may be turned on instantly and operated at a very fast on/off duty cycle to increase their lifetime.

With regard, to the exemplary integrating sphere embodiment of the present invention, integrating spheres are typically used by optical scientists and spectroscopists to (1) efficiently collect light from a light source with a random radiation pattern and (2) create a diffuse source from the light so collected. This is accomplished through multiple reflections from the highly scattering interior walls of the integrating sphere, which are inherently reflective or coated with a Lambertian scattering material. In some cases, the collection is important, such as in the characterization of light bulbs. In other cases, the goal is to create a diffuse light source, such as for spectroscopy or photochemistry applications. In these applications, the inside volume of the integrating sphere is kept as empty as possible, usually containing only air. Because of the highly scattering interior walls, and the resulting path length enhancement, several individuals have recently proposed using the integrating sphere as an enhanced sample holder for absorption spectroscopy, and as a product for characterizing samples, e.g. ocean or lake water has been characterized using this principle. During operation, while filled with a substantially or partially transparent medium, such as air (or water), the light intensity inside the integrating sphere is everywhere the same, independent of direction. This is a unique feature of the integrating sphere, provided that the optical source (or sources) are small in area as compared to the interior surface area of the integrating sphere.

In conjunction with the systems and methods of the present invention, a fluid containing a very small population of bacteria or the like is allowed to flow through the radiation filled integrating sphere. The following series of simple calculations demonstrates that, if the residence time of the fluid (e.g. water) is controlled, then the water may be disinfected using a relatively small number of commercially available UV LEDs or the like in conjunction with a properly designed integrating sphere flow cell.

UV LEDs are a relatively recent emerging technology, and are ideally suited for optimization using an integrating sphere, since they are small (e.g. microns square) as compared to the inner surface of a sphere of nominal size (e.g. 2-inch radius). Earlier UV light sources, such as mercury discharge lamps and the like, may not effectively be integrated with an integrating sphere flow cell in this manner due to their large form factor, among other considerations.

The nominal maximum flow rate of a kitchen sink, for example, is:

$$Q = 2.5 \frac{\text{gal}}{\text{min}} = 10.0 \frac{\text{qt}}{\text{min}} = 9460 \frac{\text{ml}}{\text{min}} = 158 \frac{\text{ml}}{\text{sec}}. \quad (1)$$

A proposed FIS UV LED flow cell with radius R has a volume of:

$$V = \frac{4}{3}\pi R^3. \quad (2)$$

So, if a particular flow of water Q is passing through the volume V, the average residence time of a particulate, such as a bacterium, is:

$$\tau = \frac{V}{Q}. \quad (3)$$

It is assumed that otherwise potable water is contaminated with a very small population of bacteria, at a concentration of less than about one bacterium per volume of the sphere. In the exemplary embodiment of FIGS. 1 and 2, the water flows upwards through the flow cell from a round port in the bottom of the sphere to a round port in the top of the sphere. In order to achieve a residence time for every bacterium of order τ, it is anticipated that the flow should be disrupted somewhere near mid sphere, to slow down the relatively last moving polar axial jet, and to sweep clean the relatively stagnant equatorial volume. This is illustrated in FIG. 2, by using a mechanical baffle or the like. Other methods for increasing residence time include: (1) the use of mechanical stirring; (2) the use of mechanical stirring in conjunction with non-spherical "dimples" or the like strategically located in the equatorial areas of the integrating sphere, for example; (3) utilizing directional flow via a perforated nozzle (i.e. showerhead) or the like at the water inlet; and (4) otherwise forcing the water to follow a circuitous path inside the sphere, by using a randomly bent tube, for example—the tube should be made from a UV transparent material, such as quartz or the like. The preferred way to maximize residence time may be to inject the incoming fluid into the flow cell in a direction parallel to a latitude in the southern hemisphere, for example, with the outlet perpendicular to the flow cell at the north pole, for example; this way the swirling fluid fills up the flow cell evenly from bottom to top. Optimum placement of inlet, outlet, baffles, etc. may be modeled using computational fluid dynamics (CFD). It should be noted that any non-uniformities in the integrating sphere, such as holes, dimples, baffles, etc. may degrade its optical performance. Thus, successful development of the systems and methods of the present invention requires the optimization of the trade-offs between residence time and ideal integrating sphere functionality.

If point radiation sources (e.g. UV LEDs) and receivers (i.e. bacteria, e.g e-coli bacteria) have areas that are small compared to the inside surface area of the sphere, and if the LED power is $\varphi_s$ (typically mW), radius of the sphere is R, flow rate is Q (typically cc per second), inner-surface reflectance of the sphere is k (%), reflectance is Lambertian, and f is the port fraction of the holes for sources, etc. in the sphere, then the dose per trait area delivered to a receiver (such as a bacterium) inside the sphere for each UV LED is:

$$\text{dose} = \tau\left(\frac{d\phi}{dA}\right) = \left(\frac{4\pi R^3}{3Q}\right)\left(\frac{k}{1-k(1-f)}\right)\left(\frac{\phi_s}{4\pi R^2}\right) = \frac{R\phi_s}{3Q}\left(\frac{k}{1-k(1-f)}\right). \quad (4)$$

Assume that a dose of D=5 mJ/cm² is required for bacterial disinfection. Then the number of LEDs (N) required for a sphere of reflectance k, radius R, and negligible port fraction is:

$$N = \frac{3DQ}{R\phi_s}\left(\frac{1-k}{k}\right) = \frac{98.2}{R(\text{inches})}. \quad (5)$$

Assuming a SET UV LEDs with radiant power $\varphi_s$=0.5 mW at a forward current of 20 mA, k=95% for Spectralon coating the inner surface of the sphere, and Q=158 cm³/sec as above. Then the number of LEDs to achieve the required dose is:

| Radius of integrating sphere (inches) | Number UV LEDs required (@ 0.5 mW) |
|---|---|
| 2 | 49 |
| 3 | 33 |
| 4 | 25 |
| 5 | 20 |

It should be noted that the number of required LEDs scales with 1/R and also with $1/\varphi_s$. The radiant power of available LEDs is expected to increase over the time through continuous UV materials technological developments. Likewise, the lifetime of UV LEDs is currently relatively short, on the order of about 300 hours. But LED operation may be optimized utilizing a pulsing algorithm or the like, and this lifetime is expected to continue to increase through continuous UV materials technological developments. The current generation of 0.5 mW UV LEDs consume about 100 mW of power each, so the total required system power for kitchen faucet UV water disinfection unit with a sphere of 2.5-inch radius is 2.5 watts. The power consumed by UV LEDs is also expected to continue to decrease through technological developments. By comparison, a commercially available water disinfection unit with a conventional UV mercury lamp uses 14 watts for 3 gallons per minute of flow and a 10,000 hour lamp life.

The Lambertian reflectance material must be non-toxic and highly reflecting. The sphere may be made of metal or plastic, and coated with metal, organic polymer, silicone, inorganic oxide, or anodized. Other materials are available with reasonably Lambertian characteristics, and reflectances on the order of k~90% or more (e.g. certain aluminum coatings).

As an enhancement to the systems and methods of the present invention, photocatalytic materials, such as titanium dioxide ($TiO_2$), zinc oxide, zirconium dioxide, iron oxide, aluminum oxide, Fe(III)/$Al_2O_3$, cerium oxide, manganese oxide, titanium silicates, metal substituted silicates or aluminosilicates, and any other metal oxide, mixed metal, oxide, and/or metal doped/supported metal oxide substrates (e.g. gold nanoparticles supported on silicon dioxide or titanium dioxide), or the like, may also be included inside the sphere or as part of the internal surface of the sphere to enhance photo-oxidation, photo-reduction, and the decontamination of water contaminants, including bacteria, pathogens, organic materials, halogenated compounds, biogenic compounds, metal ions, and/or biological agents. For any of these contaminants in which the direct absorbance of ultraviolet light is not possible or does not result in a decontamination, detoxification, or destruction of the contaminant, the photocatalyst inside the sphere would act as the "UV-receiver" instead of or in addition to the contaminant. Upon UV exposure, the excited photocatalyst would interact with contaminants in the water stream to purify the water. It should be noted that this process may be staged with the radiation exposure process.

Because certain UV LEDs may operate in the near-UV region of the emission spectrum, germicidal effect of the titanium dioxide ($TiO_2$) or the like may be exploited. Titanium dioxide, for example, absorbs the near-UV effectively, having a wide bandgap of 3.2 eV; this absorption resulting in a photocatalytic reaction. Absorption of UV light leads to photoexcited electrons and holes, which are powerful reducing and oxidizing agents respectively (see eq. 6). The photoexcited holes react with adsorbed water to generate highly reactive hydroxy radicals (.OH, see eq. 7). Simultaneously, the photoexcited electrons readily reduce adsorbed $O_2$ to generate superoxide radicals (.O2−, see eq. 8). These reactive oxygen species (ROS), along with various side products, such as hydrogen peroxide, are believed to contribute to cell death in photocatalytic decontamination schemes.

$$TiO_2 + hv \rightarrow TiO_2(e^- + h^+). \tag{6}$$

$$TiO_2(h^+) + H_2O_{adsorbed} \rightarrow TiO_2 + .OH_{adsorbed} + H^+. \tag{7}$$

$$TiO_2(e^-) + O_{2\ adsorbed} \rightarrow O_2^{.-}. \tag{8}$$

In accordance with the systems, and methods of the present invention, the titanium dioxide or the like is immobilized along the walls of the highly reflecting integrating sphere. Fluoropolymer represents a potential matrix for coating the inside of the sphere due to its high reflectivity in the UV, its chemical inertness, and its ability to immobilize titanium dioxide. Titanium dioxide may also be immobilized into other organic and inorganic coatings, or deposited by sputtering or electron beam deposition. However, the continuous generation of reactive oxygen species has a long-term negative effect on most immobilization substrates. In one study, the photocatalytic oxidation via titanium dioxide of a variety of polymer films and metal surfaces showed that fluoropolymer was the only substrate that was resistant to oxidation from the reactive oxygen species produced upon photoexcitation of titanium dioxide. Titanium dioxide immobilized on metal supports via a fluoropolymer binder has been shown to maintain much of its photocatalytic activity, as demonstrated via photodecomposition of 4-chlorophenol.

EXPERIMENTAL DISCUSSION

Bacterial DNA is known to have peak absorption at a wavelength of 260 nm and initial bacterial log reduction rates were determined using a planar array of 5 LEDs. The LEDs were used to irradiate a Petri dish with 20 mL of water infused with an *e-coli* strain. This set up was used to base line the dose received from UV LEDs to the standard mercury lamp sources currently used in water disinfection. A prototype FIS was also designed, built, and tested to validate the UV dose enhancement. The FIS design could hold about 230 mL of liquid and was fitted with 5 LEDs (Sphere 1) and 32 LEDs (Sphere 2). Mercury lamp source ($\lambda=254$ nm) dose requirements for 6 log reduction was found to be 30 mJ/cm². However, the NSF/ANSI 55-20072 standard requires a minimum dose of 40 mJ/cm² at 254 mm for Class A point of entry (POE) or point of use (POU) UV systems. The 5-260 nm LEDs Petri dish setup resulted in a greater than 6 log reduction in bacteria at a calculated dose of 61 mJ/cm², and a greater than 5 log reduction at 36 mJ/cm². When comparing the Petri dish configuration with 5 LEDs exposing 20 mL of bacteria laden water versus prototype Sphere 1 also with 5 LEDs exposing 230 mL of bacteria laden water, it was observed that the sphere prototype is capable of disinfecting 10 times the liquid volume of water than the Petri dish apparatus.

This comparison, along with the theoretical results, indicated that the integrating sphere prototype configuration offers an enhancement in dose over a planar array of LEDs. It should be noted that both tests started with a bacterial (*E. coli*) concentration of approximately 1E7 CFU/mL.

A 6 log reduction in *E. coli* within 3 minutes was observed using sphere 2 with 32 LEDs. The theoretical equations proposed predicted the number of required LEDs to be N=33 for a certain reflectance value k, LED power Φ, and sphere radius R. This calculation is comparable to the experimental value of N=32 used in the prototype testing.

During testing, the sphere flow cell was mechanically mixed on a slow moving orbital shaker while irradiating the bacteria infested water. Fluid dynamics modeling was performed to simulate water flow in the sphere for analysis of particle residence time. Two different models were used to investigate particle residence time and fluid flow in the sphere. Design A, the built prototype, had inlet and outlet ports horizontally aligned, while Design B had the inlet and outlet ports skewed horizontally with respect to each other. Both models had inlet and outlet pipes of 0.5-inch diameter and were modeled with a volumetric flow rate of 23.2 cm³/s, giving an inflow velocity of 0.183 m/s.

Increasing the pathlength of the fluid increased the residence time of any microorganisms in the fluid. To determine the particle residence time, 12 zero mass particles were released through the inlet pipe of the sphere and tracked over time in order to replicate the particle residence time (PRT) of microorganisms in the sphere. These simulations demonstrated Design A having a minimum PRT of 0.9 s while Design B had a minimum PRT of 1.4 s. In Design A, half of the particles were caught in an eddy current and hence not released within the first 2000 inches of travel in the sphere. Design B on the other hand, exhibited a more evenly distributed PRT with some particles revolving in eddy currents but not for longer than 50 seconds before exiting the sphere.

These results served to prove that the concept of using deep UV LEDs in an integrating sphere for water disinfection is feasible. Certification level 6 log reduction of *E. coli* bacteria in water was demonstrated in the integrating sphere flow cell prototype.

The ideal material set for the spherical flow through integrating sphere would be non-toxic, easily machine-able (so that portals may be made for fluid flow and optical sources), of sufficient mechanical integrity and strength, inexpensive, leak-proof, and mass manufacturable. Additionally, the inner surface coating of the sphere should have appropriate optical scattering properties, ideally Lambertian, and with a reflectivity of 1.0 in the deep ultraviolet. A reflectivity of 1.0 is not achievable in practice, but certain materials are close.

The standard scattering material currently used for coating surfaces in most deep UV applications is low density polytetrafluoroethylene (PTFE) inside a high reflectivity metal outer shell; PTFE acts somewhat as a diffuser, so high system reflectivity cannot be fully attained without a reflective outer layer. For a 260 nm water disinfection flow cell application, aluminum or the like provides an appropriate outer shell. Low density PTFE objects are formed by a labor intensive multistep process of (1) pressing PTFE powder into a solid form (e.g. a cube or a cylinder), (2) sintering at high temperature e.g. 500-600 degrees F., (3) machining parts with oil-fee cutting tools in a clean room environment, and (4) encapsulating in a hard mechanical metal or polymer shell. An integrating sphere is typically made by hollowing out a cube of pressed and sintered PTFE. Since low density PTFE so prepared for deep-UV scattering has a porous structure, in the proposed application it may act as an "organic sponge", picking up any contaminants (e.g. minerals, trace organics) in the flowing water, and thus the optical properties of the sphere may be adversely affected. Nevertheless, a virgin integrating sphere flow cell made from tow density PTFE provides an acceptable option in terms of optical properties, and therefore initial measurements made with such a device represent the entitlement of the system for a particular set of source power, source geometry, and inlet/outlet geometry. It should be noted that PTFE is also available in paint-on solutions with organic binders such as polyvinyl alcohol, however, these material are not as good of reflectors at wavelengths shorter than 300 nm due to absorption and degradation of the organic binder materials. The organic binders also present toxicity concerns.

Barium sulfate (BaSO4) is also an exemplary option and is commonly available in paint-on coatings which contain organic binder and solvent. Coatings from this type of material are specified to have reflectivity of 0.92 to 0.98 over the spectral range 300 nm to 1200 nm. However, for deep-UV (i.e. 260 nm), the decreasing reflectivity of the BaSO4 and the UV absorption of the organic binder combine to make BaSO4 less suitable for the current application.

Aluminum is a good candidate material for the entire integrating sphere, being a good reflector in the UV, i.e. better then e.g. silver or gold. Aluminum has been extensively used as a reflective material in the extreme UV (EUV, i.e. shorter than 200 nm) in satellite mirror applications, and after performance has degraded due to oxidation during use, the reflectance may be regenerated by over-coating with more aluminum. With a thin protective layer of e.g. magnesium fluoride ($MgF_2$), regeneration is not required, and aluminum can sustain a reflectance of around 85% at 260 nm. This is typically accomplished by sputtering a thin (e.g. half wavelength) film of $MgF_2$ onto a microns thick aluminum film that is deposited onto a surface like the inside of a spherical shell. The spherical shell might be made of aluminum, and if so the scattering can be rendered more Lambertian by roughening through e.g. "bead blasting", essentially sandblasting with glass beads before the aluminum and $MgF_2$ thin films are deposited. Aluminum and $MgF_2$ could also be deposited in a similar way onto the inner surface of a plastic sphere. Magnesium fluoride raises concerns with respect to its toxicity, though it is approved in certain small quantities by the FDA as e.g. a bonding agent for aluminum foil. It is only slightly soluble in water. Its use as a thin solid reflector coating in this water disinfection application would possibly require an extra layer of water impervious encapsulation over the exposed $MgF_2$. Another possibility would be to coat the inner Lambertian surface of an aluminum sphere with a high temperature (e.g. 600 degree F.) primer/topcoat PTFE process. Another possibility is a UV-transparent silicone hard coat on aluminum. Another possibility is anodized aluminum.

Polymers are attractive materials for flexible spherical shell prototype geometries and manufacturability, though their UV absorbance is high, and thus some kind of coating is required (e.g. aluminum, Al+$MgF_2$, PTFE, etc.) to achieve a Lambertian inner scattering surface. Rapid prototyping technology such as solid state stereolithography (SLA) and selective laser sintering (SLS) can be used to quickly and cheaply construct hollow spherical prototypes with complex geometric features using engineering thermoplastics such as Accura and Duraform (nylon), respectively. The benefit is that a large number of computer aided designs (CADs) incorporating various flow cell geometries, baffles, etc., can be first simulated using fluid dynamics software to optimize flow cell residence time. Only the best performers are thus be prototyped and evaluated. These prototypes can then be used as models to set up inexpensive injection molding processed for mass manufacturing from other thermoplastic materials and coatings, optimized for Lambertian scattering at 260 nm.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A system for disinfecting a fluid, comprising:
   a flow cell comprising one or more inlet ports and one or more outlet ports, wherein the flow cell is configured to communicate a fluid from the one or more inlet ports to the one or more outlet ports through an interior portion thereof; and
   one or more point radiation sources disposed about the flow cell, wherein the one or more point radiation sources are operable for delivering radiation to the fluid;
   wherein an interior surface of the flow cell is operable for reflecting the radiation delivered to the fluid by the one or more point radiation sources;

wherein the flow cell is an integrating cavity comprising curved and concaved opposed interior surfaces without internal corners and with all interior points visible from all other interior points;

wherein the one or more point radiation sources are disposed about a periphery of the integrating cavity;

wherein the interior surface is a Lambertian reflectance material operable for reflecting the radiation delivered to the fluid by the one or more point radiation sources and creating a diffuse source from the radiation such that a radiation intensity is uniform and independent of direction throughout the entire interior portion of the flow cell when the flow cell is filled with a substantially or partially transparent medium and the one or more point radiation sources are small in area as compared to the interior surface area of the flow cell, and a radiation energy level is equal to or less than that of the one or more point radiation sources; and wherein the interior surface and interior portion define a single flow cell corresponding to the entire integrating cavity.

2. The system of claim 1, wherein the one or more point radiation sources comprise one or more of one or more semiconductor optical sources, one or more light-emitting diode optical sources, one or more ultraviolet optical sources, and one or more deep-ultraviolet optical sources.

3. The system of claim 1, further comprising one or more mechanical baffles or stirring mechanisms disposed within the interior portion of the flow cell for selectively modifying a flow of the fluid therethrough.

4. The system of claim 1, further comprising a photocatalyzing material disposed on at least a portion of the interior surface of the flow cell.

5. The system of claim 3, further comprising a photocatalyzing material disposed on at least a portion of a surface of the one or more mechanical baffles or stirring mechanisms.

6. The system of claim 1, further comprising a controller operable for selectively activating/deactivating the one or more point radiation sources.

7. The system of claim 1, further comprising a controller operable for selectively controlling the residence time of the fluid in the interior portion of the flow cell.

8. A method for disinfecting a fluid, comprising:

providing a flow cell comprising one or more inlet ports and one or more outlet ports, wherein the flow cell is configured to communicate a fluid from the one or more inlet ports to the one or more outlet ports through an interior portion thereof; and providing one or more point radiation sources disposed about the flow cell, wherein the one or more point radiation sources are operable for delivering radiation to the fluid;

wherein an interior surface of the flow cell is operable for reflecting the radiation delivered to the fluid by the one or more point radiation sources;

wherein the flow cell is an integrating cavity comprising curved and concaved opposed interior surfaces without internal corners and with all interior points visible from all other interior points;

wherein the one or more point radiation sources are disposed about a periphery of the integrating cavity;

wherein the interior surface is a Lambertian reflectance material operable for reflecting the radiation delivered to the fluid by the one or more point radiation sources and creating a diffuse source from the radiation such that a radiation intensity is uniform and independent of direction throughout the entire interior portion of the flow cell when the flow cell is filled with a substantially or partially transparent medium and the one or more point radiation sources are small in area as compared to the interior surface area of the flow cell, and a radiation energy level is equal to or less than that of the one or more point radiation sources; and wherein the interior surface and interior portion define a single flow cell corresponding to the entire integrating cavity.

9. The method of claim 8, wherein the one or more point radiation sources comprise one or more of one or more semiconductor optical sources, one or more light-emitting diode optical sources, one or more ultraviolet optical sources, and one or more deep-ultraviolet optical sources.

10. The method of claim 8, further comprising providing one or more mechanical baffles or stirring mechanisms disposed within the interior portion of the flow cell for selectively modifying a flow of the fluid therethrough.

11. The method of claim 8, further comprising providing a photocatalyzing material disposed on at least a portion of the interior surface of the flow cell.

12. The method of claim 10, further comprising providing a photocatalyzing material disposed on at least a portion of a surface of the one or more mechanical baffles or stirring mechanisms.

13. The method of claim 8, further comprising providing a controller operable for selectively activating/deactivating the one or more point radiation sources.

14. The method of claim 8, further comprising providing a controller operable for selectively controlling the residence time of the fluid in the interior portion of the flow cell.

15. A system for disinfecting a fluid, comprising:

a flow cell comprising one or more inlet ports and one or more outlet ports, wherein the flow cell is configured to communicate a fluid comprising a biological contaminant from the one or more inlet ports to the one or more outlet ports through an interior portion thereof; and one or more point radiation sources disposed about the flow cell, wherein the one or more point radiation sources are operable for delivering radiation to the biological contaminant;

wherein an interior surface of the flow cell is operable for reflecting the radiation delivered to the biological contaminant by the one or more point radiation sources;

wherein the interior surface of the flow cell is operable for reflecting the radiation delivered to the biological contaminant by the one or more point radiation sources such that a radiation intensity is uniform and independent of direction throughout the interior portion of the flow cell when the flow cell is filled with a substantially or partially transparent medium and the one or more point radiation sources are small in area as compared to the interior surface area of the flow cell;

wherein the flow cell is an integrating cavity comprising curved and concaved opposed interior surfaces without internal corners and with all interior points visible from all other interior points;

wherein the one or more point radiation sources are disposed about a periphery of the integrating cavity;

wherein the interior surface is a Lambertian reflectance material operable for reflecting the radiation delivered to the fluid by the one or more point radiation sources and creating a diffuse source from the radiation such that a radiation energy level is equal to or less than that of the one or more point radiation sources; and wherein the interior surface and interior portion define a single flow cell corresponding to the entire integrating cavity.

16. The system of claim 15, wherein the one or more point radiation sources comprise one or more of one or more semiconductor optical sources, one or more light-emitting diode optical sources, one or more ultraviolet optical sources, and one or more deep-ultraviolet optical sources.

17. The system of claim 15, further comprising a photo-catalyzing material disposed on at least a portion of the interior surface of the flow cell.

* * * * *